United States Patent [19]
Elsener

[11] Patent Number: 5,883,022
[45] Date of Patent: Mar. 16, 1999

[54] ABSORBENT FABRIC MATERIAL OF SYNTHETIC ENDLESS FIBER

[75] Inventor: Hugo Elsener, Stabio, Switzerland

[73] Assignee: Rotecno AG, Zurich, Switzerland

[21] Appl. No.: 628,647

[22] PCT Filed: Oct. 6, 1995

[86] PCT No.: PCT/EP94/03309

§ 371 Date: Apr. 12, 1996

§ 102(e) Date: Apr. 12, 1996

[87] PCT Pub. No.: WO95/11328

PCT Pub. Date: Apr. 27, 1995

[30] Foreign Application Priority Data

Oct. 19, 1993 [DE] Germany .......................... 43 35 621.4

[51] Int. Cl.$^6$ .................................................. D03D 15/00
[52] U.S. Cl. .......................... 442/192; 442/189; 442/195; 442/203
[58] Field of Search ................................... 442/189, 192, 442/195, 203

[56] References Cited

U.S. PATENT DOCUMENTS 4,281,688 8/1981 Kelly.

FOREIGN PATENT DOCUMENTS 0269207 6/1988 European Pat. Off. .
0517687 12/1992 European Pat. Off. .

*Primary Examiner*—James J. Bell
*Attorney, Agent, or Firm*—Townsend and Townsend and Crew LLP

[57] ABSTRACT

An absorbent fabric material of synthetic endless fibers, in particular for use in clinical areas and also clean room areas and also in company and public washrooms, in which, in order to simultaneously achieve absorbent high absorbency and handling acceptance the fiber of the fabric material is texturizable and the woven material has an open woven structure in which longer non bound in thread sections (3, 6) alternate with firmly bound in thread sections (4, 5 or 7, 8 respectively) which thereby generate capillary-like interstitial spaces between the fibers.

20 Claims, 1 Drawing Sheet

ABSORBENT FABRIC MATERIAL OF SYNTHETIC ENDLESS FIBER

BACKGROUND OF THE INVENTION

1. Field of the Invention

The invention relates to an absorbent fabric material of synthetic endless fiber, and in particular to an absorbent fabric material for use in clinical areas and clean room areas, as well as in company and public washrooms.

2. Description of the Prior Art

In the clinical area, in particular in the operating theater, in just the same way as in clean rooms, the use of fabric material of natural fibers causes problems because natural fibers form fluff and lint which are carriers of germs and other contamination and which are distributed in the room's air. A further disadvantage lies in the fact that through the long drying period, swollen natural fibers, such as for example cotton, produce a favorable breeding ground for the growth of bacteria and germs.

In order to satisfy clean room conditions and requirements of hygiene, natural fiber materials are thus being increasingly avoided in the clinical area and in the clean room area and, instead, synthetic fibers are being used as much as possible. Since synthetic fibers can be manufactured as endless yarns and have a high yield strength, no fluff or lint formation arises with synthetic fabric material. It is however a disadvantage of synthetic fabric material that it is not absorbent or is only absorbent to a small degree. This disadvantage can be tolerated in the clinical area when it is used for drapes and articles of clothing, but can't be tolerated when it is used for hand towels and cloths for sucking up liquids. Thus, in spite of the disadvantages of fabric material made of natural fibers, hand towels and absorbent cloths made of cotton are used in the clinical area.

A further disadvantage of natural fabric materials lies in the fact that they have to be washed at a high temperature, in particular 95° C., with a large amount of detergent in order to remove contamination and to kill germs, whereas synthetic materials can be hygienically cleaned at a washing temperature of 60° C. and with a smaller quantity of detergent. Moreover, the energy required for drying is less with synthetic materials than with natural fabric materials since natural fabric materials pick up moisture and thereby swell, whereas the moisture only sticks to the outside of the synthetic materials.

With the synthetic materials in towel-form there is, in addition to the low absorbency, the disadvantage that these materials feel smooth and plastic-like and thus, from the point of view of their feel or handling, a lower acceptancy exists for cloths of these materials when they are to be used as hand towels which are required to be absorbent. A further disadvantage lies in the so-called "pilling effect". This is a name for a knot-like formation in which synthetic short fibers occur which, in contrast to natural fibers such as cotton fibers, do not break off under mechanical loading, but rather form knots once subjected to alternating loads.

SUMMARY OF THE INVENTION

The object of the present invention is thus to make available an absorbent material of synthetic fibers which is characterized by particular absorbency and adequate handling acceptancy.

Through the use of a texturizable fiber, which is woven into a fabric with an open woven structure, longer non-bound-in thread sections arise which alternate with firmly bound-in thread sections. These non-bound-in thread sections present between firmly bound-in thread sections enable texturizing or bulking of the texturizable fibers. With mechanical loading of the fabric material, for example when crumpling up the material when drying the hands, these thread sections are alternately extended and compressed whereby a pumping effect arises as a result of which liquid is sucked into the interstitial capillary spaces between the fibers of the fabric material. The sucked-up liquid is held back by the fabric material, in particular by adhesive forces, and thus stored. Accordingly, important for the creation of the pumping action is a plurality of free non-squashed thread sections present between two firmly bound-in crushed positions in which the fibers can be texturized.

Through the texturizing, the surface of the fibers present in the fabric increases and thereby the take-up capacity of the fabric for liquid. The liquid is thus not taken up by the fibers by swelling, as is the case with natural fibers, but rather by the fabric in that the liquid is sucked into capillary-like interstitial spaces between the fibers of the fabric material and is distributed and bound by adhesive forces.

In use the positive effect arises from the point of view of hygiene that through the rapid drying of the synthetic fabrics, the growth of bacteria and germs is reduced—the water is only bound in the interstitial spaces between the fibers and not in the swollen fiber.

Through the use of synthetic endless fibers the formation of fluff and lint is avoided with the fabric material of the invention, despite high absorbency, so that articles manufactured from this material, in particular hand towels, can be used without problem in the clinical and clean room areas. Thus, no problems exist when hand towels of this material are washed together with other synthetic towels such as drapes or articles of clothing. If cotton hand towels are jointly washed with these other articles, then the fluff and lint originating from the cotton hand towels also stick to the remaining articles and must be laboriously removed therefrom, as a rule by hand.

A further advantage lies in the fact that cloths of the material of the invention have a lower washing temperature and require a lesser amount of detergent and also less drying energy. Cloths of the material of the invention can thus be used particularly economically.

In accordance with one form of the invention, approximately 60% to 80% and preferably about 70% of the thread crossing points are not bound in. A fabric of this kind combines a high absorbency with good handling acceptancy. This results from the fact that, with the given ratio of bound-in to non-bound-in thread crossing points, adequate free thread sections are present which increase the absorbency, on the one hand, and, on the other hand, an adequate number of bound-in thread crossing points are present in order to achieve good non-slip properties and to pronouncedly structure the fabric surface.

In accordance with a further embodiment of the present invention, the bound-in thread crossing points are firmly fixed, and more specifically during the dying process. In this way the ideal fabric structure is advantageously fixed and thereby the absorbency and the handling acceptancy are permanently ensured.

In accordance with a further embodiment of the present invention, the fabric is formed out of a multi-filament fiber. A fiber of this kind has a particularly large surface and the interstitial spaces between the fibers are particularly fine, whereby the absorbency of the fabric material formed therefrom is increased. A multi-filament fiber can moreover be made particularly texturizable whereby the pumping effect of the fabric is increased.

The texturizing of the multi-filament fiber preferably takes place in accordance with a further embodiment of the present invention by crimping, i.e. by twisting individual filaments under the influence of temperature during the manufacture of the multi-filament. A highly texturizable material such as a false twist extruded or friction extruded polyester yarn is preferably used for the manufacture of the fabric.

In accordance with a further embodiment of the present invention, the individual filaments have a thickness of 0.5 dtex to 5 dtex, in particular of 1 dtex to 2.5 dtex, i.e. grams per 10,000 m.

With this layout the fabric has, on the one hand, a very large surface and, on the other hand, a high number of capillary spaces between the fibers. The yarn formed from the multi-filament thereby preferably has a thickness of 50 dtex to 500 dtex and fibers of different thicknesses can also be used in one fabric.

In accordance with a further embodiment of the invention the fibers are hydrophilically finished or dressed, and more specifically by chemical means. In this way the absorbency and the storage capacity of the fabric are advantageously increased.

In accordance with a further embodiment of the present invention, the fibers or the fabric formed by the fibers are antistatically finished or dressed. A fabric treated in this way has the advantage that it is not only itself free of fluff and lint-free, but rather also does not attract any foreign fluff or lint as a result of electrostatic charging.

In accordance with a further embodiment of the present invention, the fabric has conductive fibers, and more specifically fibers of the same mechanical characteristics as the non-conductive fibers. In this way an electrostatic charging-up of the fabric material is advantageously avoided. Alternatively, individual filaments of each fiber can be made conductive.

In accordance with a further embodiment of the present invention, the filaments of the fibers of the fabric of the invention can also have triangular, rectangular or polygonal cross-sections, as well as a round or oval cross-section. Through such cross-section the absorbency of the fabric material of the invention can be further increased since in this way a surface structure is generated which promotes the pick-up of liquid.

A further way of promoting the pick-up capability can also be brought about in accordance with a further embodiment of the present invention by structuring the surface of the fiber filament of the fabric of the invention itself. Liquid adhering to the fabric, in particular in droplet form, is sucked up more easily by the fabric as a result of this design of the fibers since the roughness of the surface reduces the surface tension and thereby promotes a distribution of the droplet.

Hand towels, in particular in the clinical area and clean room area, as well as roller hand towels in public and company areas, represent a preferred manner of using the fabric material of the invention. Roller hand towels in the commercial area, in particular in restaurants and public houses, are very frequently washed so that the economical advantages are particularly notable here.

DETAILED DESCRIPTION OF THE PREFERRED EMBODIMENTS

Figure 1:
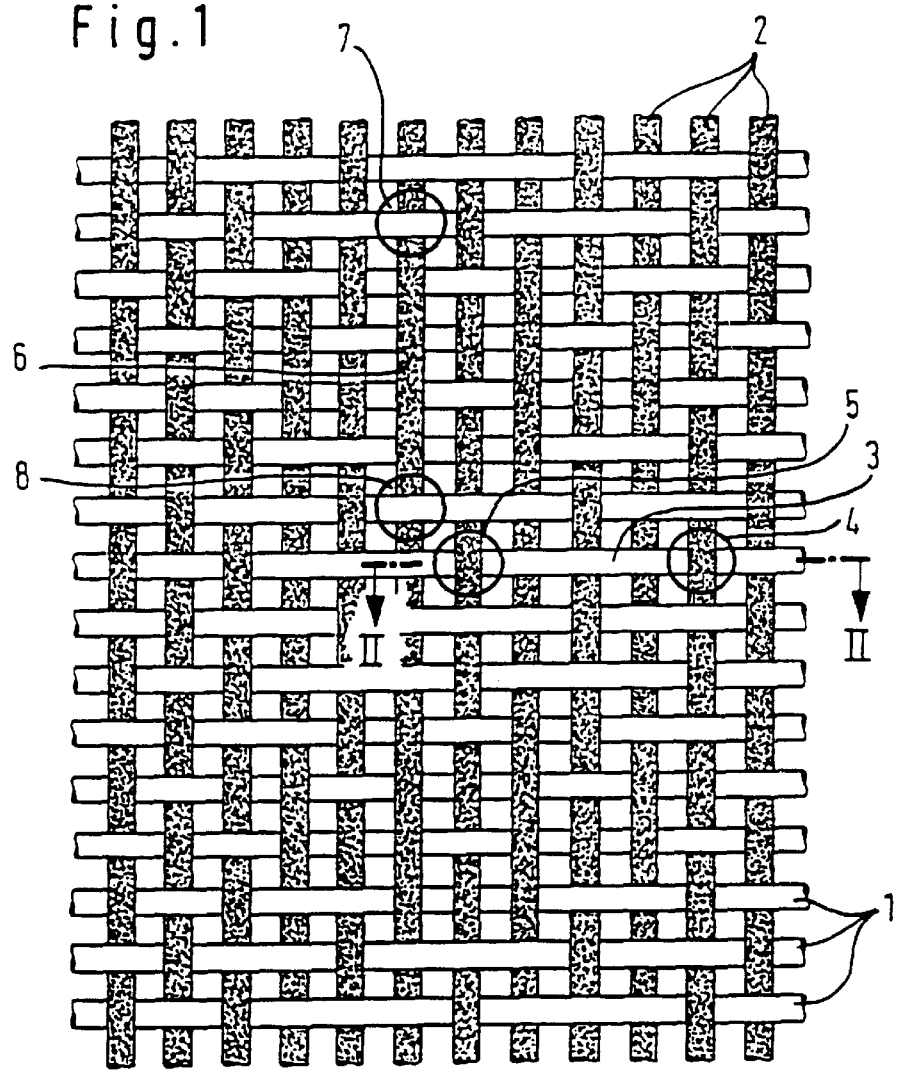
FIG. 1 is a schematic view of a fabric structure in accordance with the present invention shown in an enlarged schematic illustration.

In the fabric structure shown in FIG. 1, warp threads 1 are shown in white and weft threads 2 which extend perpendicular thereto are shown in black. The illustrated structure shows a plurality of non-bound-in thread sections, such as for example warp thread section 3 which is bound in between firmly bound-in thread sections such as warp thread sections 4 and 5. Such non-bound-in thread sections are also present amongst the weft threads 2, for example the thread section 6 between the firmly bound-in regions 7 and 8. Through this design a high absorbency of the fabric is achieved in association with a pronounced structuring of the fabric surface.

Figure 2:
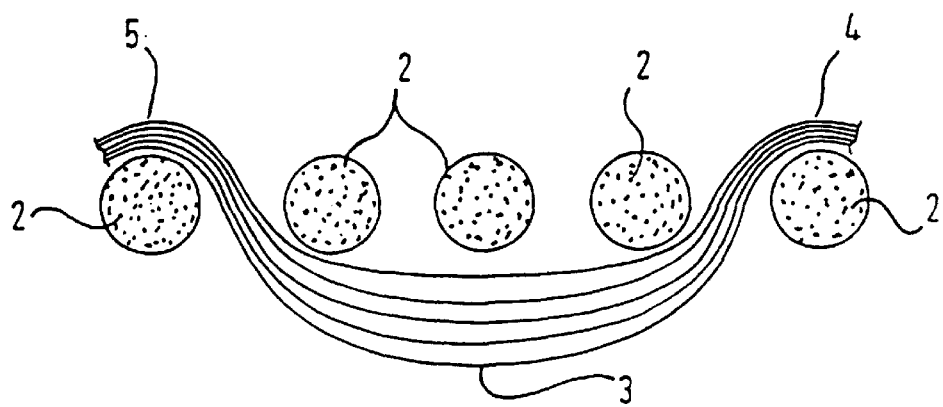
FIG. 2 is a sectional view through a fabric in accordance with the invention corresponding to the line II—II in FIG. 1 in a greatly simplified representation.

The section through a tissue in accordance with the invention shown in FIG. 2 shows in a greatly simplified sideview a non-bound-in warp thread section 3 which is located between two firmly bound-in warp thread sections 4 and 5. In this non-bound-in thread section 3 the warp thread 1 is texturized or bulked up, whereas it is crushed in the firmly bound-in sections 4 and 5. Through a mechanical loading of the fabric both the warp threads 1 and also the weft threads 2 are moved relative to one another. The non-bound-in region 3 of the warp thread 1 is thereby alternately more strongly and more weakly bulked up or texturized, whereby a pumping action arises which sucks in liquid into the intermediate spaces between the individual filaments of the warp thread 1. The liquid is also firmly held in the intermediate spaces by capillary and adhesive forces and thereby stored in the fabric. The same occurs in the non-bound-in regions of the weft threads so that on the whole a greater quantity of liquid can be sucked up and stored.

The warp and weft threads preferably can have a thickness of between 50 dtex to 500 dtex and for example the warps can have 76 dtex and the wefts 167 dtex. The individual filaments preferably can have a thickness between 0.5 dtex to 5 dtex and preferably individual filaments can be used in the individual titer range from 1 dtex to 2.5 dtex. The number of filaments in a thread can for example amount to 128.

A fabric material manufactured in the above recited manner is particularly suitable for the manufacture of hand towels because its handling corresponds to that of hand towels of natural fabric. In particular, these can be hand towels such as are used in the clinical area and in roller hand towel apparatuses.

Through crimping of the multi-filament fibers, a random assembly arises and thereby a multi-filament yarn with a plurality of internal hollow cavities which are accessible from the outside and which can serve to take up liquid. Through the crimping there arises a crimped yarn with, e.g., a length of 9,000 m from a multi-filament which was originally 10,000 m long.

What is claimed is:

1. Absorbent woven material comprising interwoven warp and weft yarns consisting of synthetic endless fibers for use in clinical areas, clean room areas, and company and public washrooms, wherein the fibers of the woven material can be bulked and wherein the woven material has an open woven structure in which longer not bound-in sections of yarn alternate with firmly bound-in sections of yarn.

2. Woven material in accordance with claim 1, wherein the woven material has approximately 60% to 80% not bound-in yarn crossing points.

3. Woven material in accordance with claim 2, wherein said yarn crossing points are thermally fixed.

4. Woven material in accordance with claim 1, wherein said synthetic endless fibers are crimped.

5. Woven material in accordance with claim 1, wherein said yarns comprise a false twist extruded yarn.

6. Woven material in accordance with claim 1, wherein the individual fibers have a thickness in the range of 0.5 dtex to 5 dtex, i.e. grams per 10,000 m.

7. Woven material in accordance with claim 1, wherein the synthetic endless fibers forming a yarn have a total thickness in the range of 50 dtex to 500 dtex.

8. Woven material in accordance with claim 1, wherein synthetic endless fibers of different thicknesses are used in one fabric.

9. Woven material in accordance with claim 1, wherein the synthetic endless fiber is hydrophilic.

10. Woven material in accordance with claim 1, wherein the synthetic endless fiber is antistatic.

11. Woven material in accordance with claim 1, wherein the woven material contains conductive fibers.

12. Woven material in accordance with claim 1, wherein said fibers have cross-sections selected from the group, comprising triangular, rectangular, polygonal round and oval cross-sections.

13. Woven material in accordance with claim 1, wherein said fibers have a structured surface.

14. Woven material in accordance with claim 1, wherein said yarn comprises a polyester yarn.

15. Woven material in accordance with claim 11, wherein at least some of the conductive fibers comprise conductive filaments.

16. Woven material in accordance with claim 11, wherein said conductive fibers comprise carbon fibers.

17. Woven material in accordance with claim 6, wherein said individual fibers have a thickness in the range of 1 dtex to 2.5 dtex.

18. Woven material in accordance with claim 9, wherein said synthetic endless fiber has been chemically treated to render it hydrophilic.

19. Woven material in accordance with claim 11, wherein said conductive fibers have substantially the same mechanical characteristics as said synthetic endless fibers.

20. A h and_towel comprising a woven material wherein the woven material is in accordance with any one of the claims 1 to 13, 14, 17 or 18.

* * * * *